(12) United States Patent
Mohseni

(10) Patent No.: US 12,186,577 B2
(45) Date of Patent: Jan. 7, 2025

(54) METHODS AND SYSTEMS FOR EFFICIENT COUPLING OF LIGHT FROM OUTSIDE TISSUE TO SMALL VOLUMES INSIDE TISSUE

(71) Applicant: Northwestern University, Evanston, IL (US)

(72) Inventor: Hooman Mohseni, Wilmette, IL (US)

(73) Assignee: Northwestern University, Evanston, IL (US)

( * ) Notice: Subject to any disclaimer, the term of this patent is extended or adjusted under 35 U.S.C. 154(b) by 642 days.

(21) Appl. No.: 17/274,500

(22) PCT Filed: Sep. 9, 2019

(86) PCT No.: PCT/US2019/050150
§ 371 (c)(1),
(2) Date: Mar. 9, 2021

(87) PCT Pub. No.: WO2020/055718
PCT Pub. Date: Mar. 19, 2020

(65) Prior Publication Data
US 2022/0047886 A1    Feb. 17, 2022

Related U.S. Application Data

(60) Provisional application No. 62/730,099, filed on Sep. 12, 2018.

(51) Int. Cl.
*A61N 5/06*    (2006.01)

(52) U.S. Cl.
CPC .... *A61N 5/0613* (2013.01); *A61N 2005/0626* (2013.01); *A61N 2005/063* (2013.01);
(Continued)

(58) Field of Classification Search
CPC .......... A61N 5/0613; A61N 2005/0626; A61N 2005/0665
See application file for complete search history.

(56) References Cited

U.S. PATENT DOCUMENTS

| 6,366,388 B1 * | 4/2002 | Hampp | ................. G02F 1/0126 |
| | | | 359/275 |
| 7,519,406 B2 | 4/2009 | Blank et al. | |

(Continued)

OTHER PUBLICATIONS

The International Search Report and the Written Opinion issued on Nov. 19, 2019 for International Patent Application No. PCT/US2019/050150; pp. 1-7.
Hassani et al., "Evaluation of the Returned Electromagnetic Signal from Retrorefectors in Turbid Media," Scientific Reports, 2019, vol. 9: 6550; pp. 1-7.

(Continued)

*Primary Examiner* — Yingchuan Zhang
*Assistant Examiner* — Jessica L Mullins
(74) *Attorney, Agent, or Firm* — Bell & Manning, LLC

(57) ABSTRACT

A system to couple light to tissue includes a first light source configured to emit first light of a first wavelength lambda $\lambda_1$ and a second light source configured to emit second light of a second wavelength $\lambda_2$. The system also includes a retro-modulator configured to receive the first light and the second light. The retro-modulator is configured to modulate the first light of the first wavelength $\lambda_1$ based at least in part on an intensity of the second light of the second wavelength $\lambda_2$. The retro-modulator is also configured to reflect the modulated first light for use in generation of a guide-star within the tissue.

13 Claims, 4 Drawing Sheets

(52) U.S. Cl.
CPC ............... *A61N 2005/0658* (2013.01); *A61N 2005/0665* (2013.01)

(56) References Cited

U.S. PATENT DOCUMENTS

| | | |
|---|---|---|
| 8,475,506 B1 | 7/2013 | Bendett et al. |
| 9,360,428 B2 | 6/2016 | Tao et al. |
| 2009/0054955 A1 | 2/2009 | Kopell et al. |
| 2010/0262212 A1 | 10/2010 | Shoham et al. |
| 2011/0108707 A1 | 5/2011 | Cui et al. |
| 2016/0073887 A1 | 3/2016 | Lee et al. |
| 2016/0259059 A1 | 9/2016 | Mohseni |

OTHER PUBLICATIONS

Horstmeyer et al., "Guidestar-assisted wavefront-shaping methods for focusing light into biological tissue," *Nat. Photonics*, 2015, vol. 9, pp. 563-571.

Yotam Gil et al., "Feasibility of retroreflective transdermal optical wireless communication," *Applied Optics*, Jun. 20, 2012, vol. 51, No. 18; pp. 4232-4239.

Hongki Kang et al., "Feasibility Study of Extended-Gate-Type Silicon Nanowire Field-Effect Transistors for Neural Recording," *Sensors* 2017, vol. 17, No. 705; pp. 1-15. DOI: 10.3390/s17040705.

Samuel G. Rodriques et al., "Multiplexed neural recording along a single optical fiber via optical reflectometry," *Journal of Biomedical Optics* (May 2016), vol. 21, No. 5; pp. 057003-1-057003-11.

The Non-Final Office Action issued on Oct. 13, 2021 for U.S. Appl. No. 16/638,218; pp. 1-21.

\* cited by examiner

METHODS AND SYSTEMS FOR EFFICIENT COUPLING OF LIGHT FROM OUTSIDE TISSUE TO SMALL VOLUMES INSIDE TISSUE

CROSS-REFERENCE TO RELATED APPLICATION

The present application is a National Stage of International Application No. PCT/US19/50150, filed Sep. 9, 2019, which claims the priority benefit of U.S. Provisional Patent Application No. 62/730,099, filed Sep. 12, 2018, the entire disclosures of which are incorporated by reference herein.

BACKGROUND

Light presents the most efficient method of communication and energy transfer that humans have discovered. Light transmissions can be used for a diverse array of applications, such as networking, medical treatment, stimulation, analysis, high bandwidth communication, etc. As one example, light can be used to interact with human/animal tissue for the purpose of analyzing/imaging the tissue, communicating with the tissue and/or devices (e.g., medical implants) associated with the tissue, treating the tissue, etc. Light can also be used to study brain activity, monitor neurons in the central or the peripheral nervous system, and develop high bandwidth brain-machine interfaces.

SUMMARY

An illustrative system to couple light to tissue includes a first light source configured to emit first light of a first wavelength $\lambda_1$ and a second light source configured to emit second light of a second wavelength $\lambda_2$. The system also includes a retro-modulator configured to receive the first light and the second light. The retro-modulator is configured to modulate the first light of the first wavelength $\lambda_1$ based at least in part on an intensity of the second light of the second wavelength $\lambda_2$. The retro-modulator is also configured to reflect the modulated first light for use in generation of a guide-star within the tissue.

An illustrative method for coupling light includes transmitting first light of a first wavelength $\lambda_1$ from a first light source and second light of a second wavelength $\lambda_2$ from a second light source. The first light and the second light are transmitted to a retro-modulator. The method also includes modulating, by a modulator of the retro-modulator, the first light of the first wavelength $\lambda_1$ based at least in part on an intensity of the second light. The method also includes reflecting, by a reflector of the retro-modulator, the modulated first light. The method further includes generating a guide-star within tissue based at least in part on the reflected, modulated first light.

Other principal features and advantages of the disclosure will become apparent to those skilled in the art upon review of the following drawings, the detailed description, and the appended claims.

BRIEF DESCRIPTION OF THE DRAWINGS

Illustrative embodiments of the disclosure will hereafter be described with reference to the accompanying drawings, wherein like numerals denote like elements.

DETAILED DESCRIPTION

Figure 1:
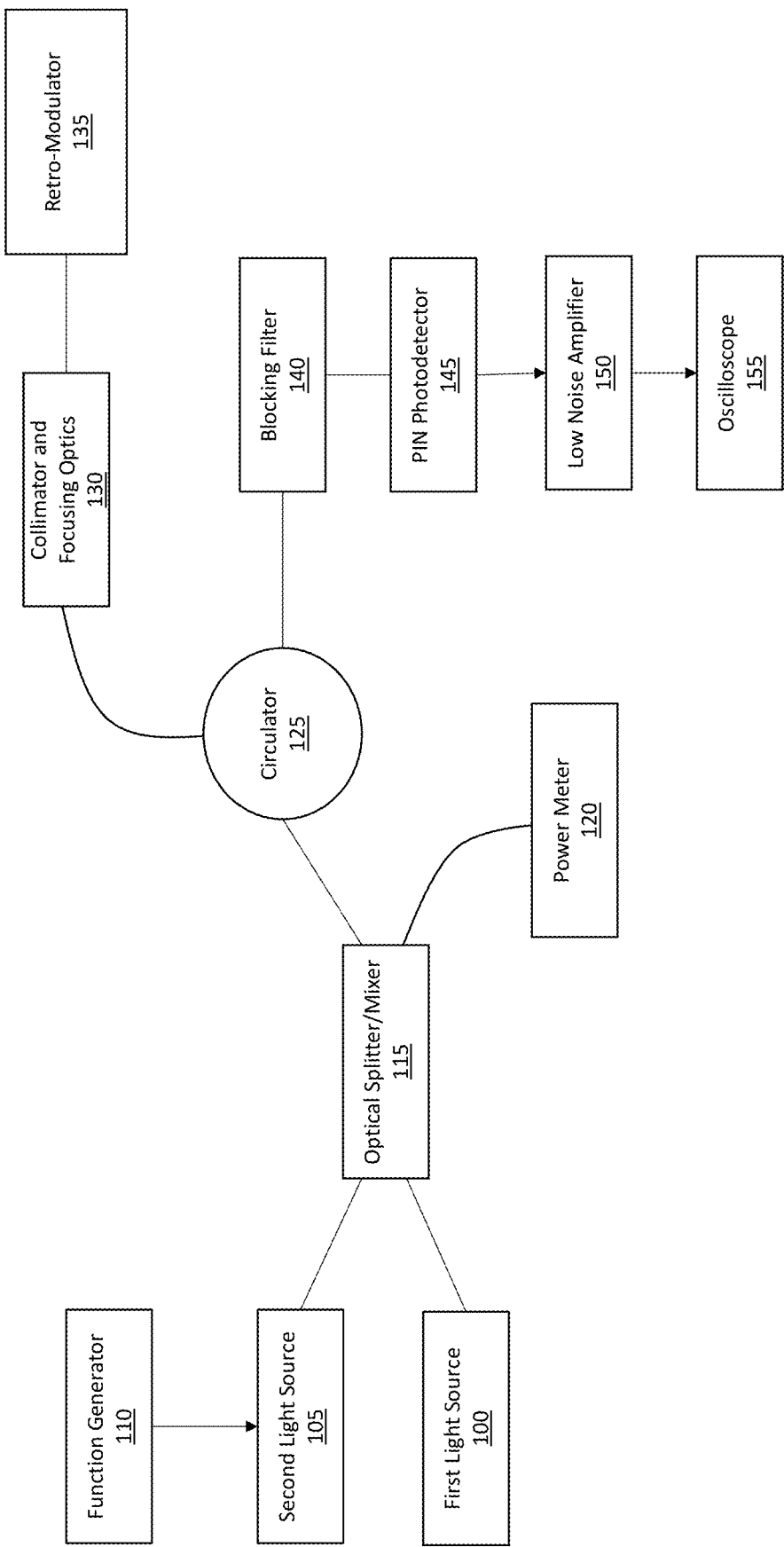
FIG. 1 is a block diagram of a system to couple light from outside of tissue to one or more small volumes inside of the tissue in accordance with an illustrative embodiment.

Efficient coupling of light from outside tissue to small (focused) volumes inside tissue is extremely important for many applications, including optical imaging, data communication, neural stimulation, neural signal reading, optical heating, optogenetics, and energy transmission through tissue. A major challenge in achieving such efficient coupling is the high scattering coefficient of human (and animal) tissue. Conventional methods for coupling light within tissue are based on focusing an ultrasound beam to modulate a wavelength of interest. However, ultrasound cannot be easily focused to a diameter smaller than about 50 μm.

Described herein are methods and systems for coupling light from outside tissue to a small volume inside tissue. Specifically, the proposed systems and methods can produce very small points that modulate a wavelength of interest, and thus can achieve very high coupling efficiency when the volume of interest is very small. The methods and systems are based in part on using adaptive optics and a guide-star. In some embodiments, one or more retro-modulators can be used. A retro-modulator can refer to an electroabsorption (EA) quantum well modulator sandwiched between p-doped and n-doped cladding layers, with a reflector (or retroreflector) attached to its back. The retro-modulators can have very small lateral dimensions, e.g., no more than about 0.5 micrometers (μm). In some embodiments, the lateral dimensions of the retromodulators are no more than about 1 μm, no more than about 10 μm, no more than about 100 μm, no more than about 500 μm, or in the range of from about 0.5 μm to about 500 μm. Other dimensions can be used for the retro-modulators in alternative embodiments such as 0.1 μm, 0.05 μm, etc.

Since enhancement of energy at a focusing spot is approximately proportional to the number of adaptive optical elements (e.g., spatial light modulator(s), micro-mirror array(s), etc.) present divided by the number of modes within a guide-star volume, reducing the guide-star volume increases coupling enhancement. A retro-modulator having lateral dimensions of about 0.5 μm is about 100 times smaller than that of a focused ultrasound beam. Using such a retro-modulator, the system can produce modulating spots (i.e., guide stars) that are 0.5 um or smaller, which as noted above is ~100 times smaller than can be achieved using ultrasound. The result is an enhancement of energy by about $10^4$ to $10^6$ for the proposed system as compared to existing systems. In addition, the proposed system can achieve modulation depth values of about 3% to about 35% (including 5%, 10%, 15%, 20%, 25%, and 30%), which is about 100 to 1000 times better than that of a focused ultrasound beam, resulting in a higher signal-to-noise ratio. Additionally, the convergence speed in adaptive optics of the proposed system and the coupling enhancement are significantly better than in traditional systems. The proposed system also enables use a wide range of modulation frequencies, including up into the gigahertz range.

The proposed system is based in part on a combination of a single-mode or multi-mode modulator and a reflector or retro-reflector on its backside. In one embodiment, the modulator modulates the light intended for coupling with a wavelength ($\lambda_1$), using another light that is at a different wavelength ($\lambda_2$). In order to evaluate the efficiency of the above-described system, an experimental setup was used. FIG. 1 is a block diagram of a system to couple light from outside of tissue to one or more small volumes inside of the tissue in accordance with an illustrative embodiment. The system includes a first light source 100 and a second light source 105. The first light source 100 can be a tunable laser source having a tunable wavelength range of 1480 nanometers (nm) to 1580 nm in one embodiment. In an illustrative embodiment, the first light source 100 generates a probe light that has a wavelength of 1550 nm ($\lambda_1$). Alternatively, a different type of light and/or wavelength range may be used for the first light source 100.

The second light source 105 can be a distributed feedback (DFB) laser configured to transmit modulated laser light having a wavelength of 1300 nanometers (nm) ($\lambda_2$). Alternatively, a different type of light source and/or wavelength may be used for the second light source 105. The second light source is connected to a function generator 110, which can be a 50 KiloHertz (KHz) square wave generator in one embodiment. Alternatively, a different wave type and/or frequency may be used by the function generator 110. The function generator 110 is used to modulate the second light in accordance with the wave type and frequency of the function generator 110. An optical splitter/mixer 115 is used to receive light from the first light source 100 and the second light source 105, and to direct the received light to a circulator 125. A power meter 120 is connected to the optical splitter/mixer 115, and can be used to monitor and/or control the power/intensity of the first light and the second light.

The circulator 125 is an optical component that includes a plurality of inputs/output ports, and that is designed to receive light at a first port and direct the light out through an adjacent port. For example, light received at a first port of the circulator 125 is output through a second port, light received through the second port is output through a third port, and so on. In the embodiment of FIG. 1, the circulator 125 is designed to pass the received light from the first light source 100 and the second light source 105 on to a collimator and focusing optics 130. The collimator is used to form the light into parallel beams, and the focusing optics can include one or more lenses, one or more mirrors/reflectors, etc. that are used to direct and focus the light toward a retro-modulator 135. In some embodiments, the retro-modulator can include an electroabsorption modulator and a single reflector (or retro-reflector). The single reflector can be in the form of a gold (Au) mirror, in one embodiment. The electroabsorption modulator can be processed to form electrically isolated islands of various sizes that share the single reflector. The retro-reflector is used to reflect modulated light from the EA modulator back to a filter and measurement setup, as described below.

In alternative embodiments, the retro-modulator can include a plurality of EA modulators that are configured to generate a plurality of guide-stars in proximity to one another. The plurality of EA modulators can be accompanied by a corresponding plurality of reflectors in one embodiment, or by a single reflector that reflects modulated light from all of the EA modulators in an alternative embodiment.

The absorbed light at 1300 nm (i.e., the light from the second light source 105) produces electron-hole pairs in the electroabsorption modulator portion of the retro-modulator 135, which are then swept to the n-doped and p-doped regions surrounding the quantum-well region of the electroabsorption modulator, respectively. These charges produce a voltage change across the quantum well region that is similar to the 'open-circuit voltage' of a solar cell. This voltage produces an electric field that modulates the transition energy of the quantum wells due to the quantum-confined Stark shift, and hence changes their absorption coefficient at 1550 nm, which is the wavelength of the light from the first light source 100 (i.e., the probe light).

Modulated light from the modulator reflects off of the reflector/retro-reflector of the retro-modulator 135, and travels back through the collimator and focusing optics 130 to the circulator 125. Light of the second wavelength (i.e., from the second light source 105) can also be reflected by the reflector/retro-reflector. The circulator directs the reflected light to a blocking filter 140, which is configured to block reflected light from the second light source 105. For example, in embodiments where light from the second light source 105 has a wavelength of 1300 nm, the blocking filter 140 can be configured to block the wavelength 1300 nm. In alternative embodiments, different wavelength value(s) may be used for the light and blocking filter. The unblocked portions of the reflected light are passed from the blocking filter 140 to a PIN photodetector 145. In some embodiments, the PIN photodetector 140 can be an indium gallium arsenide p-i-n device. The light is passed from the PIN photodetector 140 to a low noise amplifier 150, and on to an oscilloscope 155 for analysis, manipulation, storage, etc.

Figure 2:
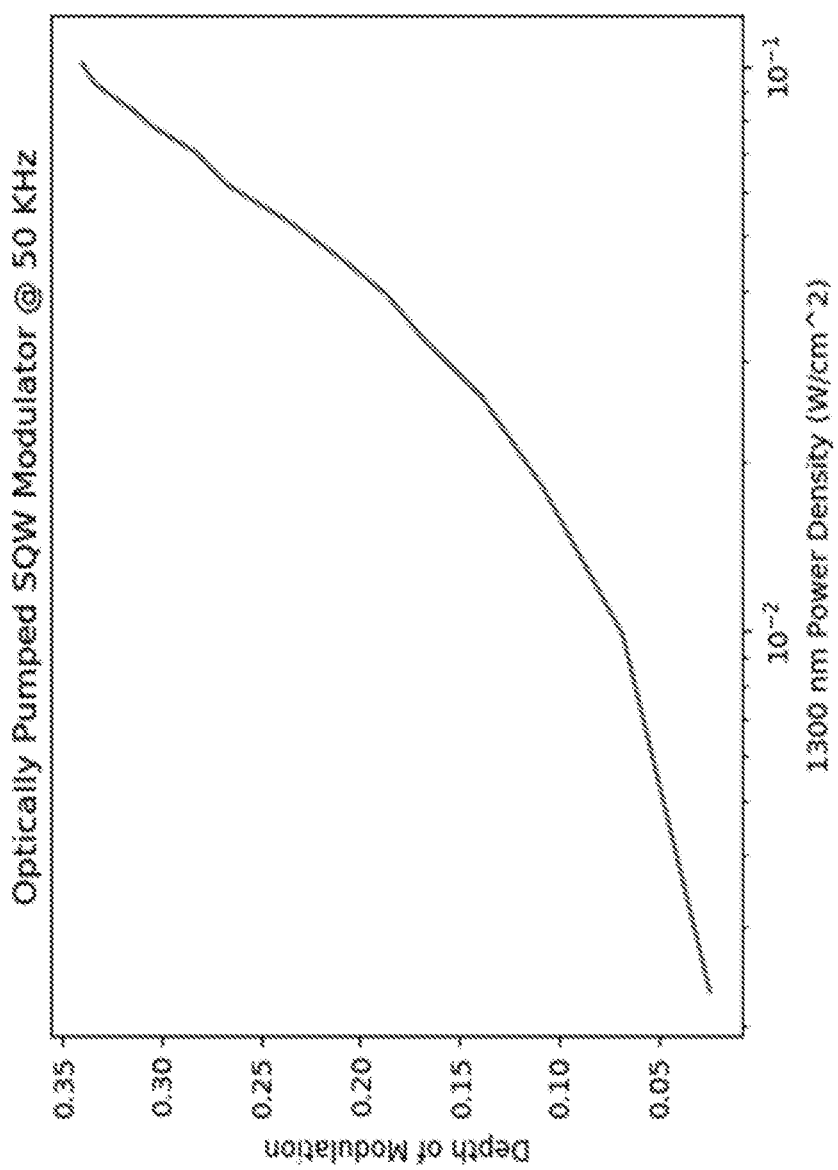
FIG. 2 depicts the depth of modulation resulting from the system of FIG. 1 in accordance with an illustrative embodiment.

The test system of FIG. 1 was used to determine the depth of modulation of light as a function of the power density of the light. FIG. 2 depicts the depth of modulation resulting from the system of FIG. 1 in accordance with an illustrative embodiment. More specifically, FIG. 2 shows the measured depth of modulation at wavelength $\lambda_1$=1550 nm versus the modulating laser power density at wavelength $\lambda_2$=1300 nm, where the modulation frequency was 50 KHz. The depth of modulation is defined as:

$$\text{Depth of Modulation} = \frac{s_H - s_L}{s_H}, \quad \text{Eq. 1}$$

where $S_H$ refers to the modulated returned signal at its high value, and $S_L$ refers to the modulated returned signal at its low value.

Figure 3:
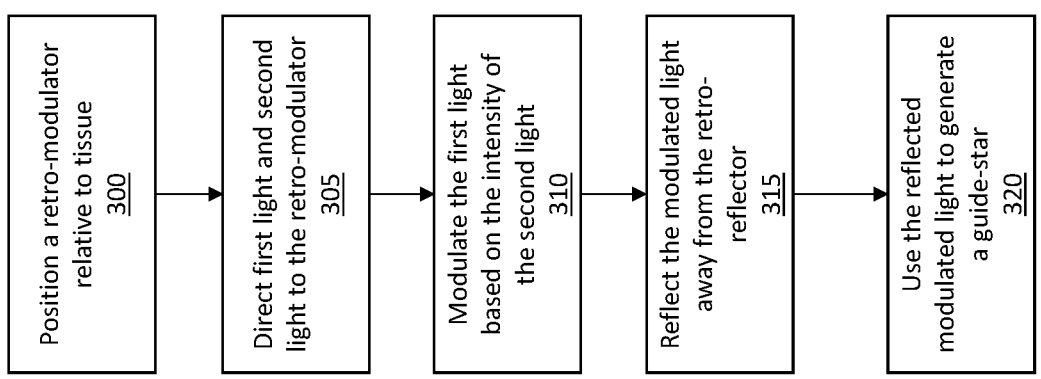
FIG. 3 is a flow diagram depicting operations performed by a light coupling system in accordance with an illustrative embodiment.

FIG. 3 is a flow diagram depicting operations performed by a light coupling system in accordance with an illustrative embodiment. In alternative embodiments, fewer, additional, and/or different operations may be performed. Also, the use of a flow diagram is not meant to be limiting with respect to the order of operations performed. In an operation 300, a retro-modulator is positioned relative to tissue. The term tissue can refer to biological material (e.g., skin, muscles, epithelial tissue, connective tissue, nerves, brain tissue, etc.) of a human or animal patient. The patient may be a healthy patient or a patient having a disease, e.g., cancer. The retro-modulator can be wholly or partially implanted within the tissue in an illustrative embodiment. Alternatively, the retro-modulator can be placed into contact with or adjacent to a surface of the tissue.

The retro-modulator can include an electroabsorption (EA) modulator and a reflector/retro-reflector optically coupled to the EA modulator. The EA modulator may be a surface normal electroabsorption modulator, and may be single mode or multi-mode, depending on the embodiment.

In an illustrative embodiment, the EA modulator can be formed from a first doped layer of semiconductor, a second doped layer of semiconductor having opposite polarity to the first doped layer, and an active layer positioned between the first doped layer and the second doped layer. The active layer can be a multi-quantum well (MQW) active layer in one embodiment. For example, the active layer can be configured as a superlattice structure comprising multiple sublayers of semiconductor material that is configured to provide alternating quantum wells and barriers. The EA modulator is configured (e.g., by selection of the composition, thickness, and number of sublayers in its active layer) so that its operating wavelength corresponds to a wavelength $\lambda_1$. This means that at zero or low voltage across the active layer, transmission of light having the wavelength $\lambda_1$ is high (e.g., at its maximum). As noted above, the lateral (i.e., in-plane) dimensions of the EA modulator may be relatively small. Similarly, the lateral dimensions of the reflector may be of the same small scale.

In an operation 305, first light and second light are directed to the retro-modulator. The first light can have a wavelength $\lambda_1$ and the second light can have a wavelength $\lambda_2$, where the wavelength $\lambda_2$ is less than the wavelength $\lambda_1$. As discussed above, the EA modulator has an operating wavelength $\lambda_1$. In an illustrative embodiment, the wavelength $\lambda_1$ is the wavelength of light to be coupled into the tissue, and the intensity of the second light having wavelength $\lambda_2$ is controlled to modulate the first light, as described in more detail below. The second light having the wavelength $\lambda_2$ can be modulated, e.g., in the range of from about 1 MHz to about 10 GHz. Alternatively, a different modulation frequency can be used. The first light and the second light can originate from respective light sources, which can be lasers in an illustrative embodiment. In alternative implementations, different light source(s) may be used, such as light-emitting diodes, etc.

The particular wavelengths $\lambda_1$, $\lambda_2$ used for the first light and the second light depend upon the desired application. For example, different wavelengths can be used for different types of tissue, to achieve different depths of modulation, based on the specifics of the modulator, etc. By way of illustration, the wavelengths $\lambda_1$, $\lambda_2$ may be within the near-infrared region of the electromagnetic spectrum (i.e., from about 750 nm to about 1 μm) or the short-wave-infrared region (i.e., from about 1 μm to about 2.5 μm). Alternatively, different wavelengths may be used. Similarly, the composition of the material layers of the electroabsorption modulator depend upon the desired application. By way of illustration, the semiconductors used for the material layers may be group III/V alloys (e.g., binary, ternary, quaternary alloys). Alternatively, other semiconductor materials may be used.

In an operation 310, the system modulates the first light based on the intensity of the second light. Specifically, as the applied voltage across the active layer of the modulator increases, the absorption edge of the active layer is red-shifted according to the bulk or quantum-confined stark effect and transmission of the first light having the wavelength $\lambda_1$ decreases. This allows for the modulation of the first light. In the present method, since the wavelength $\lambda_2$ is less than the wavelength $\lambda_1$, the electroabsorption modulator can absorb the second light having the wavelength $\lambda_2$ being transmitted to it. The intensity of the second light having the wavelength $\lambda_2$ controls the density of electrons and holes in the first and second doped layers (based on the carrier lifetime) of the EA modulator. Therefore, the intensity of the second light having the wavelength $\lambda_2$ modulates the charge accumulation and, hence, the voltage across the active layer. This change of voltage effectively modulates the transmission of light having the wavelength $\lambda_1$ through the electroabsorption modulator. Thus, the light having the wavelength $\lambda_2$ is being used to modulate the light having the wavelength $\lambda_1$.

The system reflects the modulated light away from the retro-reflector in an operation 315. In an illustrative embodiment, the reflector portion of the retroreflector is optically coupled to the electroabsorption modulator such that it reflects light (e.g., modulated light having the wavelength $\lambda_1$) being transmitted through the electroabsorption modulator and incident on a surface of the reflector back through the electroabsorption modulator, e.g., back outside the tissue. The reflector may be a film of a reflective material, (e.g., gold), a microsphere having a surface coated with a reflective material, an hourglass lens having a surface coated with a reflective material, corner cubes, etc. In an illustrative embodiment, the reflector can be in direct contact with a surface of the electroabsorption modulator.

In an operation 320, the system utilizes the reflected modulated light to generate a guide-star, which is a small volume spot/point of modulated light that can penetrate deep into the tissue. In some embodiments, the system can include one or more detectors and/or a computing system to analyze the modulated reflected light, determine a path traveled by the light, etc. Based on this analysis, the system can transmit light along the path such that the light does not scatter, but instead forms a guide-star, which can be used for any of the applications described herein.

A system that utilizes a single retro-modulator can produce very efficient and compact guide-stars. However, such a system cannot produce a plurality of different guide-stars that are close to each other, since the guide-stars would all show the same modulation frequency. In an alternative embodiment, a plurality of retro-modulators can be used. Each retro-modulator in the plurality of retro-modulators can include an EA modulator. For example, an array of EA modulators may be used. In some embodiments, each of the individual EA modulators may have a different configuration (e.g., size, operating wavelength, etc.). Alternatively, some (or all) of the EA modulators may have the same configuration. In some embodiments, each individual electroabsorption modulator may be optically coupled to an individual reflector. Alternatively, some (or all) of the electroabsorption modulators may share a single reflector.

In an embodiment with multiple retro-modulators, one or more oscillator circuits can be used to achieve self-oscillation of retro-modulators at different frequencies. By way of illustration, to produce a desired frequency at each retro-modulator, a compact oscillator circuit (e.g., a circuit that includes two transistors) may be used. In one embodiment, the oscillators can use optical power, produced by the electroabsorption modulator, to power up the oscillators. Besides using transistors, other types of circuits and methods may be used in alternative embodiments, including any self-oscillating device or material.

Figure 4:
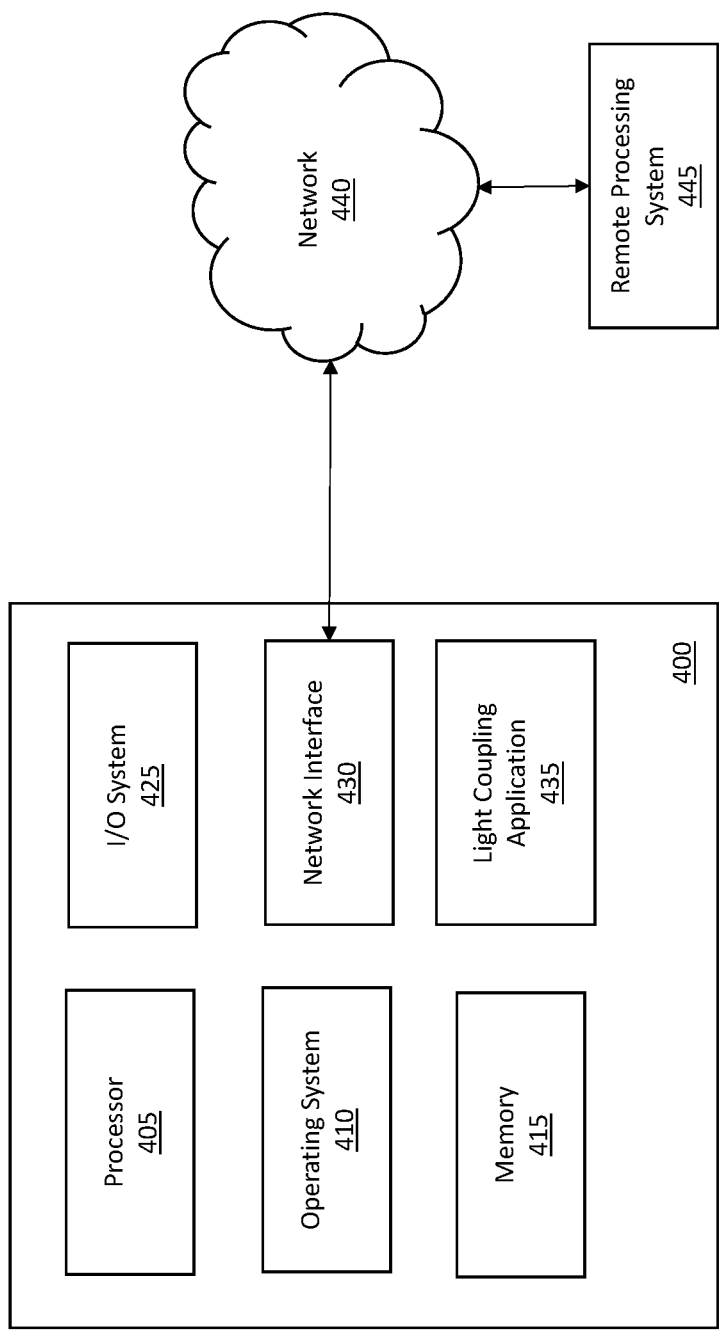
FIG. 4 is a block diagram of a computing system for a light coupling system in accordance with an illustrative embodiment.

FIG. 4 is a block diagram of a computing system 400 for a light coupling system in accordance with an illustrative embodiment. The computing system 400 includes a processor 405, an operating system 410, a memory 415, an I/O system 425, a network interface 430, and a light coupling application 435. In alternative embodiments, the computing system 400 may include fewer, additional, and/or different components. The components of the computing system 400 communicate with one another via one or more buses or any other interconnect system. In an illustrative embodiment, the computing system 400 can be part of a laptop computer, desktop computer, tablet, a photodetector, an oscilloscope, etc.

The processor 405 can be any type of computer processor known in the art, and can include a plurality of processors and/or a plurality of processing cores. The processor 405 can include a controller, a microcontroller, an audio processor, a graphics processing unit, a hardware accelerator, a digital signal processor, etc. Additionally, the processor 405 may be implemented as a complex instruction set computer processor, a reduced instruction set computer processor, an x86 instruction set computer processor, etc. The processor 405 is used to run the operating system 410, which can be any type of operating system.

The operating system 410 is stored in the memory 415, which is also used to store programs, network and communications data, peripheral component data, light coupling data such as wavelength information, material information, material dimensions, the light coupling application 435, and other operating instructions. The memory 415 can be one or more memory systems that include various types of computer memory such as flash memory, random access memory (RAM), dynamic (RAM), static (RAM), a universal serial bus (USB) drive, an optical disk drive, a tape drive, an internal storage device, a non-volatile storage device, a hard disk drive (HDD), a volatile storage device, etc.

The I/O system 425 is the framework which enables users and peripheral devices to interact with the computing system 400. The I/O system 425 can include a mouse, a keyboard, one or more displays, a speaker, a microphone, etc. that allow the user to interact with and control the computing system 400. The I/O system 425 also includes circuitry and a bus structure to interface with peripheral computing devices such as power sources, USB devices, peripheral component interconnect express (PCIe) devices, serial advanced technology attachment (SATA) devices, high definition multimedia interface (HDMI) devices, proprietary connection devices, etc. In an illustrative embodiment, the I/O system 425 is configured to receive inputs and operating instructions from the user.

The network interface 430 includes transceiver circuitry that allows the computing system to transmit and receive data to/from other devices such as remote computing systems, servers, websites, etc. The network interface 430 enables communication through the network 440, which can be in the form of one or more communication networks and devices. For example, the network 440 can include a cable network, a fiber network, a cellular network, a wi-fi network, a landline telephone network, a microwave network, a satellite network, etc. and any devices/programs accessible through such networks. The network interface 430 also includes circuitry to allow device-to-device communication such as Bluetooth® communication.

The light coupling application 435 includes hardware and/or software, and is configured to perform any of the operations described herein. Software of the light coupling application 435 can be stored in the memory 415. As an example, the light coupling application 435 can include computer-readable instructions to turn the light sources of the system on and off. The light coupling application 435 can also include computer-readable instructions to adjust/control a wavelength of the light sources, to adjust/control an intensity of the light sources, to control a photodetector that receives reflected modulated light, to analyze the reflected modulated light, to generate one or more guide-stars in tissue based on the reflected modulated light, etc.

The computing system 400 is in communication with a remote processing system 445 via the network 440. In an illustrative embodiment, the remote processing system 445 can be used to perform any of the processing operations described herein. For example, the remote processing system 445 can be used to analyze reflected modulated light, determine location(s) for guide-star placement, analyze results of guide-star placement, etc. In some embodiments, the remote processing system 445 can house some or all of the light coupling application 435. In an alternative embodiment, the remote processing system 445 may not be used.

Applications for the present methods and systems include, but are not limited to, brain-machine interfaces (or brain-computer interfaces), cancer treatments using optical beams, photodynamic therapy, optical imaging through tissue, optical data communication through tissue, neural stimulation, neural signal reading, optical heating, optogenetics, energy transmission through tissue, high bandwidth communication with medical implants, etc.

The word "illustrative" is used herein to mean serving as an example, instance, or illustration. Any aspect or design described herein as "illustrative" is not necessarily to be construed as preferred or advantageous over other aspects or designs. Further, for the purposes of this disclosure and unless otherwise specified, "a" or "an" means "one or more."

The foregoing description of illustrative embodiments of the disclosure has been presented for purposes of illustration and of description. It is not intended to be exhaustive or to limit the disclosure to the precise form disclosed, and modifications and variations are possible in light of the above teachings or may be acquired from practice of the disclosure. The embodiments were chosen and described in order to explain the principles of the disclosure and as practical applications of the disclosure to enable one skilled in the art to utilize the disclosure in various embodiments and with various modifications as suited to the particular use contemplated. It is intended that the scope of the disclosure be defined by the claims appended hereto and their equivalents.

What is claimed is:

1. A system to couple light to tissue, the system comprising:
    a first light source configured to emit first light of a first wavelength $\lambda 1$;
    a second light source configured to emit second light of a second wavelength $\lambda 2$;
    a splitter/mixer configured to receive the first light and the second light and to pass the received first light and second light to a circulator; and
    a retro-modulator configured to receive the first light and the second light, wherein the retro-modulator is configured to:
    modulate the first light of the first wavelength $\lambda 1$ based at least in part on an intensity of the second light of the second wavelength $\lambda 2$; and
    reflect the modulated first light to generate a guide-star within the tissue.

2. The system of claim 1, wherein the retro-modulator is in contact with the tissue.

3. The system of claim 1, wherein the retro-modulator comprises an electroabsorption modulator and a reflector optically coupled to the electroabsorption modulator.

4. The system of claim 3, wherein the electroabsorption modulator has an operating wavelength of the first wavelength $\lambda 1$.

5. The system of claim 1, wherein the second wavelength $\lambda 2$ is less than the first wavelength $\lambda 1$.

6. The system of claim 1, further comprising a power meter connected to the splitter/mixer and configured to monitor or control the intensity of the second light.

7. The system of claim 1, further comprising the circulator, wherein the circulator is configured to receive the first light and the second light from the splitter/mixer and direct the first light and the second light to one or more optical components.

8. The system of claim 7, wherein the one or more optical components include a collimator and a focusing lens that are configured to focus the first light and the second light onto the retro-modulator.

9. The system of claim 7, wherein the circulator is further configured to receive the reflected modulated first light and reflected second light from the retro-modulator and to direct the reflected modulated first light and the reflected second light to a blocking filter.

10. The system of claim 9, wherein the blocking filter is configured to block light of the second wavelength $\lambda 2$.

11. The system of 11, further comprising a photodetector configured to receive the reflected modulated first light from the blocking filter.

12. The system of claim 1, wherein the retro-modulator includes a plurality of modulators, and further comprising a plurality of oscillators configured to perform self-oscillation of the plurality of modulators at different frequencies.

13. A system to couple light to tissue, the system comprising:
- a first light source configured to emit first light of a first wavelength $\lambda 1$;
- a second light source configured to emit second light of a second wavelength $\lambda 2$;
- a function generator configured to modulate the second light of the second wavelength $\lambda 2$, wherein the function generator includes a square wave generator; and
- a retro-modulator configured to receive the first light and the second light, wherein the retro-modulator is configured to:
- modulate the first light of the first wavelength $\lambda 1$ based at least in part on an intensity of the second light of the second wavelength $\lambda 2$; and
- reflect the modulated first light to generate a guide-star within the tissue.

* * * * *